(12) United States Patent
Sookraj

(10) Patent No.: US 10,500,104 B2
(45) Date of Patent: Dec. 10, 2019

(54) BIODEGRADABLE SANITARY ARTICLES WITH HIGHER BIOBASED CONTENT

(71) Applicant: Novomer, Inc., Waltham, MA (US)

(72) Inventor: Sadesh H. Sookraj, Cambridge (ZA)

(73) Assignee: Novomer, Inc., Boston, MA (US)

( * ) Notice: Subject to any disclaimer, the term of this patent is extended or adjusted under 35 U.S.C. 154(b) by 424 days.

(21) Appl. No.: 15/369,886

(22) Filed: Dec. 6, 2016

(65) Prior Publication Data

US 2018/0153746 A1 Jun. 7, 2018

(51) Int. Cl.
| | |
|---|---|
| *A61F 13/15* | (2006.01) |
| *A61F 13/515* | (2006.01) |
| *A61F 13/514* | (2006.01) |
| *A61F 13/472* | (2006.01) |
| *A61L 15/42* | (2006.01) |
| *A61L 15/60* | (2006.01) |
| *A61L 15/62* | (2006.01) |
| *A61F 13/51* | (2006.01) |

(52) U.S. Cl.
CPC ...... *A61F 13/15252* (2013.01); *A61F 13/472* (2013.01); *A61F 13/515* (2013.01); *A61F 13/51401* (2013.01); *A61L 15/425* (2013.01); *A61L 15/60* (2013.01); *A61L 15/62* (2013.01); *A61F 13/51* (2013.01); *A61F 2013/51028* (2013.01); *A61F 2013/51035* (2013.01)

(58) Field of Classification Search
CPC .................................................. A61F 13/15252
See application file for complete search history.

(56) References Cited

U.S. PATENT DOCUMENTS

| | | | |
|---|---|---|---|
| 4,988,344 A | 1/1991 | Reising et al. | |
| 5,026,589 A * | 6/1991 | Schechtman | A61F 13/51 428/138 |
| 5,185,009 A | 2/1993 | Sitnam | |
| 5,350,624 A * | 9/1994 | Georger | D04H 1/56 139/420 B |
| 5,759,569 A | 6/1998 | Hird et al. | |
| 6,258,869 B1 | 7/2001 | Shah et al. | |
| 8,445,703 B2 | 5/2013 | Allen et al. | |
| 8,796,475 B2 | 8/2014 | Allen et al. | |
| 9,096,510 B2 | 8/2015 | Porcelli et al. | |
| 9,156,803 B2 | 10/2015 | Allen et al. | |
| 9,173,780 B2 | 11/2015 | Buell et al. | |
| 9,206,144 B2 | 12/2015 | Allen et al. | |
| 9,327,280 B2 | 5/2016 | Lee et al. | |
| 9,375,358 B2 | 6/2016 | Ehnsperger et al. | |
| 9,375,507 B2 | 6/2016 | Tian et al. | |
| 9,403,788 B2 | 8/2016 | Lee et al. | |
| 9,440,220 B2 | 9/2016 | Naumann et al. | |
| 9,445,951 B2 | 9/2016 | Moberg-Alehammer et al. | |
| 9,474,657 B2 | 10/2016 | Berrizbeitia et al. | |
| 9,480,968 B2 | 11/2016 | Weismantel et al. | |
| 9,493,391 B2 | 11/2016 | Allen et al. | |
| 9,738,784 B2 | 8/2017 | Allen et al. | |
| 9,914,689 B2 | 3/2018 | Porcelli et al. | |
| 10,065,914 B1 | 9/2018 | Ruhl et al. | |
| 10,099,988 B2 | 10/2018 | Farmer et al. | |
| 10,099,989 B2 | 10/2018 | Sookraj | |
| 10,144,802 B2 | 12/2018 | Sookraj | |
| 10,221,150 B2 | 3/2019 | Farmer et al. | |
| 10,221,278 B2 | 3/2019 | Lee et al. | |
| 10,245,559 B2 | 4/2019 | Lapointe et al. | |
| 2004/0030283 A1* | 2/2004 | Brooks | A61F 13/0203 604/48 |
| 2004/0078015 A1* | 4/2004 | Copat | A61F 13/51 604/370 |
| 2010/0003517 A1* | 1/2010 | Hansson | A61F 13/53 428/373 |
| 2011/0015602 A1* | 1/2011 | Schmidt | A61F 13/51121 604/367 |
| 2011/0319849 A1 | 12/2011 | Collias et al. | |
| 2012/0123137 A1 | 5/2012 | Allen et al. | |
| 2012/0157950 A1* | 6/2012 | Geilich | A61F 13/5116 604/366 |

(Continued)

FOREIGN PATENT DOCUMENTS

| | | |
|---|---|---|
| WO | 2010/118128 A1 | 10/2010 |
| WO | 2012/030619 A1 | 3/2012 |

(Continued)

OTHER PUBLICATIONS

Kadkin et al., Polyester Polyols: Synthesis and Characterization of Diethylene Glycol Terephthalate Oligomers, Polyester Polyols, 1114-1123; Jan. 2003 (10 pages).

(Continued)

*Primary Examiner* — Adam Marcetich
*Assistant Examiner* — Jessica R Arble
(74) *Attorney, Agent, or Firm* — Morrison & Foerster LLP

(57) ABSTRACT

The present invention is directed to sanitary articles such as disposable diapers, adult incontinent pads, feminine hygiene products, and sanitary napkins comprised of biodegradable polymers with higher biobased content. The sanitary articles include a topsheet, an absorbent core, and a backsheet. The topsheet is comprised of biodegradable polyester polyol polymer foam which may be configured to wick liquid away from a wearer's body and may be impregnated with superabsorbent polymer. The absorbent core may be comprised of superabsorbent polymer including a cross-linked and/or partially neutralized polyacrylic acid polymer, cross-linked polyacrylic acids or cross-linked starch-acrylic acid graft polymers. The backsheet may be comprised of poly-lactone polymers having generally hydrophobic characteristics. In preferred embodiments, the polymeric materials comprising the topsheet, absorbent core, and backsheet are formed from raw materials with high biobased content.

22 Claims, No Drawings

(56) References Cited

U.S. PATENT DOCUMENTS

| | | |
|---|---|---|
| 2013/0165670 A1 | 6/2013 | Allen et al. |
| 2013/0209775 A1 | 8/2013 | Allen et al. |
| 2013/0281715 A1 | 10/2013 | Allen et al. |
| 2014/0275575 A1 | 9/2014 | Allen et al. |
| 2014/0296522 A1 | 10/2014 | Lee et al. |
| 2014/0309399 A1 | 10/2014 | Porcelli et al. |
| 2015/0005513 A1 | 1/2015 | Lee et al. |
| 2015/0141693 A1 | 5/2015 | Allen et al. |
| 2015/0299083 A1 | 10/2015 | Porcelli et al. |
| 2015/0342799 A1 | 12/2015 | Michiels et al. |
| 2015/0368394 A1 | 12/2015 | Allen |
| 2016/0016876 A1 | 1/2016 | Mahoney |
| 2016/0102040 A1 | 4/2016 | Allen et al. |
| 2016/0102068 A1 | 4/2016 | Allen et al. |
| 2016/0288057 A1 | 10/2016 | Lapointe et al. |
| 2017/0029352 A1 | 2/2017 | Sookraj et al. |
| 2017/0073463 A1 | 3/2017 | Lee et al. |
| 2017/0080409 A1 | 3/2017 | Farmer et al. |
| 2017/0096407 A1 | 4/2017 | Sookraj |
| 2017/0107103 A1 | 4/2017 | Sookraj et al. |
| 2017/0145126 A1 | 5/2017 | Mahoney |
| 2017/0224540 A1* | 8/2017 | Li .................... A61F 13/49011 |
| 2017/0225157 A1 | 8/2017 | Lee |
| 2017/0247309 A1 | 8/2017 | Porcelli et al. |
| 2017/0267618 A1 | 9/2017 | Sookraj et al. |
| 2018/0016219 A1 | 1/2018 | Farmer et al. |
| 2018/0022677 A1 | 1/2018 | Sookraj |
| 2018/0029005 A1 | 2/2018 | Sookraj |
| 2018/0030014 A1 | 2/2018 | Sookraj et al. |
| 2018/0030015 A1 | 2/2018 | Farmer et al. |
| 2018/0030201 A1 | 2/2018 | Farmer et al. |
| 2018/0057619 A1 | 3/2018 | Sookraj |
| 2018/0094100 A1 | 4/2018 | Farmer et al. |
| 2018/0155490 A1 | 6/2018 | Sookraj |
| 2018/0155491 A1 | 6/2018 | Sookraj |
| 2018/0282251 A1 | 10/2018 | Sookraj |
| 2018/0305286 A1 | 10/2018 | Sookraj |
| 2018/0305289 A1 | 10/2018 | Sookraj et al. |
| 2018/0354881 A1 | 12/2018 | Farmer et al. |
| 2018/0354882 A1 | 12/2018 | Sookraj |
| 2019/0002385 A1 | 1/2019 | Sookraj |
| 2019/0030520 A1 | 1/2019 | Lee |
| 2019/0031592 A1 | 1/2019 | Sookraj et al. |
| 2019/0047972 A1 | 2/2019 | Sookraj |
| 2019/0071538 A1 | 3/2019 | Sookraj |
| 2019/0076834 A1 | 3/2019 | Sookraj |
| 2019/0076835 A1 | 3/2019 | Sookraj |
| 2019/0106532 A1 | 4/2019 | Sookraj |

FOREIGN PATENT DOCUMENTS

| | | |
|---|---|---|
| WO | 2012/051219 A2 | 4/2012 |
| WO | 2012/158573 A1 | 11/2012 |
| WO | 2013/063191 A1 | 5/2013 |
| WO | 2013/122905 A1 | 8/2013 |
| WO | 2013/126375 A1 | 8/2013 |
| WO | 2014/004858 A1 | 1/2014 |
| WO | 2014/008232 A2 | 1/2014 |
| WO | 2015/085295 A2 | 6/2015 |
| WO | 2015/138975 A1 | 9/2015 |
| WO | 2015/171372 A1 | 11/2015 |
| WO | 2015/184289 A1 | 12/2015 |
| WO | 2016/015019 A1 | 1/2016 |
| WO | WO 2016/023016 | 2/2016 |
| WO | 2016/130947 A1 | 8/2016 |
| WO | 2016/130977 A1 | 8/2016 |
| WO | 2016/130988 A1 | 8/2016 |
| WO | 2016/130993 A1 | 8/2016 |
| WO | 2016/130998 A1 | 8/2016 |
| WO | 2016/131001 A1 | 8/2016 |
| WO | 2016/131003 A1 | 8/2016 |
| WO | 2016/131004 A1 | 8/2016 |
| WO | 2017/023777 A1 | 2/2017 |
| WO | 2017/023820 A1 | 2/2017 |
| WO | 2017/165323 A1 | 9/2017 |
| WO | 2017/165344 A1 | 9/2017 |
| WO | 2017/165345 A1 | 9/2017 |
| WO | 2018/085251 A1 | 5/2018 |
| WO | 2018/085254 A1 | 5/2018 |
| WO | 2018/106824 A1 | 6/2018 |
| WO | 2018/107185 A1 | 6/2018 |
| WO | 2018/136638 A1 | 7/2018 |
| WO | 2018/144998 A1 | 8/2018 |
| WO | 2018/170006 A1 | 9/2018 |
| WO | 2018/200466 A1 | 11/2018 |
| WO | 2018/200471 A1 | 11/2018 |
| WO | 2019/006366 A1 | 1/2019 |
| WO | 2019/006377 A1 | 1/2019 |
| WO | 2019/050649 A1 | 3/2019 |
| WO | 2019/051184 A1 | 3/2019 |
| WO | 2019/070981 A1 | 4/2019 |

OTHER PUBLICATIONS

International Search Report and Written Opinion dated Apr. 23, 2018 regarding International Application No. PCT/US2017/064943 filed Dec. 6, 2017 (11 pages).

* cited by examiner

BIODEGRADABLE SANITARY ARTICLES WITH HIGHER BIOBASED CONTENT

FIELD OF THE INVENTION

The present invention relates to novel sanitary articles such as disposable diapers, adult incontinence pads, sanitary napkins and the like, comprised of biodegradable polymers having higher biobased content. Specifically, the present invention provides for sanitary articles including a liquid pervious topsheet, a liquid impervious backsheet, an absorbent core, elastic members, and adhesive fasteners comprised of polymers having higher biodegradability and biobased content. Advantageously, the present invention provides for more environmentally responsible sanitary applications.

BACKGROUND OF THE INVENTION

Generally, a polymer is a larger molecule comprised of multiple repeated smaller molecules known as monomers. During a process known as polymerization, the monomers may be covalently bonded to each other forming larger polymer chains. The composition and arrangement of the monomers may determine the characteristics of the polymer, for example, determining the biodegradability and biobased content of the polymer.

The biobased content of the polymer relates to the raw material sources from which the monomers are derived. Specifically, the degree of biobased content depends on the amount of carbons in the monomers which are derived from biological, recycled, renewable, or otherwise sustainable materials. Such biological materials may include sources such as crop residues, wood residues, grasses, municipal solid waste, and algae. A polymer with higher biobased content may be preferable for use in sustainable and environmentally responsible applications.

Biodegradable polymers may also be beneficial in environmentally responsible applications. Biodegradable polymers generally include a main chain comprised of bonded organic molecules which may decompose by natural processes into smaller environmentally compatible molecules. The specific chemical composition of the monomers in the biodegradable polymers will determine what smaller molecules are produced by decomposition, the mechanisms by which decomposition occurs, and the rate at which decomposition occurs.

Many conventional polymers may not be comprised of monomers which confer characteristics of biodegradability or some degree of biobased content. In addition, modifying conventional processes to produce environmentally responsible polymers may be costly, require long production cycles, and/or be difficult to modify.

Generally, sanitary articles such as disposable diapers, adult incontinence pads, feminine hygiene products, and sanitary napkins include an absorbent core to receive and retain liquids. For absorbent articles to function efficiently, the absorbent core must quickly acquire liquids into the structure, preferably wicking the liquids away from the body of the wearer with a specialized topsheet layer. The liquids may easily penetrate the topsheet and be absorbed by the absorbent core. The retained fluids may also not penetrate a hydrophobic backsheet which is positioned farthest from a wearer's body.

The topsheet is generally compliant, soft feeling, and non-irritating to the wearer's skin while maintaining a liquid pervious characteristic, permitting liquids to readily penetrate through its thickness. A conventional topsheet may be manufactured from a wide range of materials, such as porous foams, reticulated foams, apertured plastic films, natural fibers (e.g., wood or cotton fibers), synthetic fibers (e.g., polyester or polypropylene fibers) or from a combination of natural and/or synthetic fibers. Conventionally, the topsheet is made of a material intended to isolate the wearer's skin from liquids contained in the absorbent core.

The backsheet is generally impervious to liquids and is conventionally manufactured from a thin plastic film, such as polypropylene or polyethylene, although other materials may also be used. The backsheet prevents the fluids which are absorbed and contained in the absorbent core from soiling articles of clothing which contact the sanitary article such as bedsheets and undergarments. Similar to the topsheet, the back sheet is generally flexible and compliant to readily conform to the general shape and contours of the wearer's body.

The absorbent core is generally positioned between the topsheet and the backsheet to form the sanitary article. The absorbent core is generally compressible, conformable, non-irritating to the wearer's skin, and capable of absorbing and retaining liquids and certain body excretions. The absorbent core may conventionally comprise laminates or combinations of several sheets or webs of the requisite type of materials.

There exists a need for improved biodegradability of sanitary articles. The present invention solves this need by providing for sanitary articles comprised of polymeric material having increased biodegradability and biobased content.

SUMMARY OF THE INVENTION

The present invention is directed to sanitary articles that provide multiple benefits over those currently available by minimizing the impact of such articles to the environment while at the same time improving the comfort of such articles to the user. Accordingly, one benefit is a sanitary article comprised of biodegradable polymers with high biobased content that minimizes the damage of these articles to the environment. In addition, the incorporation of highly absorbent materials into the topsheet in accordance with this invention reduces the feeling of moisture against the skin of those that use sanitary articles.

In one embodiment the invention is a sanitary article having a topsheet, backsheet, and absorbent core. The topsheet is comprised of a heterogeneous physical mixture of biodegradable polyester polyol polymer and, relative to the mass of the polyester polymer, a lesser mass of a superabsorbent polymer dispersed through the topsheet as discrete particles. The absorbent core comprises a biodegradable superabsorbent polymer having an inner side positioned adjacent to and fixed with respect to said topsheet. The backsheet comprises a biodegradable and liquid impermeable polymer positioned adjacent to an outer side of said absorbent core and fixed with respect to said absorbent core.

In another aspect of the invention the topsheet may comprise a biodegradable polyester polyol polymer having a lattice that retains the superabsorbent particles.

In another aspect the lattice may comprise pores that are impregnated with the superabsorbent polymer to provide the heterogenous dispersion of biodegradable superabsorbent polymer.

The topsheet will have an absorbent face that is positioned next to the absorbent core and a corporeal face that faces the outside of the sanitary article and the concentration of superabsorbent polymer may be greater near the corporeal face relative to the concentration near the absorbent face or concentration of superabsorbent polymer may be greater near the absorbent face relative to the concentration near the corporeal face.

In some aspects of the invention, one or more polyester polyols, poly-lactones, and/or polyacrylic acid derivatives may be used to form biodegradable elastic members. In some embodiments one or more polyester polyols, poly-lactones, and/or polyacrylic acid derivatives may be used to form biodegradable adhesive fasteners.

In other aspects the topsheet may comprise a biodegradable polyester polyol polymer in the form of a foam with superabsorbent particles interspersed therein as a physical mixture. The foam may be comprised of a lattice in which the superabsorbent particles are dispersed. In other embodiments the foam may define pores that are impregnated with a heterogenous dispersion of biodegradable superabsorbent polymer.

Suitable polyester polyol polymers for the topsheet include multiple carbonyl, carbonate, acetal, ether, nitrile, urethane, urea, imide, anhydride, phosphate, and/or cyanocrylate functional groups in the main chain for facilitating biodegradability. The polyol may include cross-links between polymer main chains allowing for the formation of pores in a three-dimensional structure. The composition of the polyol and the cross-linking molecules may determine the pore size and general structural properties of the polyol lattice. The pore size and general structural properties of the polyol lattice may determine a capacity for superabsorbent polymer and inter-lattice dispersion distance for superabsorbent polymer.

In other aspects of the invention the biodegradable superabsorbent foam is produced in at least two steps including polymerization of the polyol and foaming of the lattice while impregnating the superabsorbent polymer within the pores of the lattice.

In preferred embodiments, the backsheet of the present invention includes poly-lactone, polybutylene succinate, and/or polybutylene succinate derivatives. In certain preferred embodiments, the backsheet may be comprised of poly-lactone polymers comprising β-lactone monomers and having linear chains of repeating monomer units containing carbon and oxygen atoms provided by a β-lactone feed produced from the carbonylation of an epoxide containing carbon atoms that originate from a renewable source. In some embodiments, the poly-lactone polymers include cross-linking agents such as vinyl groups, for example, N,N'-methylene-bisacrylamide, N,N'-ethylene-bis-methacrylamide, hexamethylene-bis-acrylamide, triallyl amine, ethylene glycol dimethacrylate, trimethylolpropane trimethacrylate, pentaerythritol trimethacrylate, and ally methacrylate. In certain preferred embodiments, the poly-lactones may have or be modified to have a higher degree of hydrophobicity.

In certain preferred embodiments of the present invention, the absorbent core may have an inner side positioned proximate to a topsheet and an outer side positioned proximate to a backsheet and may be comprised of polyacrylic acid derivatives. In preferred aspects of the invention the materials for the absorbent core are produced by novel methods and processes which impart a high biobased content characteristic on the absorbent core. The methods and processes for producing acrylic acid from β-propiolactone involve polymerizing β-propiolactone with an ionic initiator in a reactor to produce a polymer intermediate with a polyacrylic acid backbone and a plurality of polypropiolactone side chains. Advantageously, the biodegradable polyacrylic acid derivatives formed may have higher biobased content.

In some aspects, provided are polymers produced according to any of the methods described herein.

In some variations of the foregoing, the polymers have a bio-content of greater than 0%, and less than 100%. In certain variations of the foregoing, the polymers have a bio-content of at least 10%, at least 20%, at least 30%, at least 40%, at least 50%, at least 60%, at least 70%, at least 80%, at least 90%, at least 95%, at least 96%, at least 97%, at least 98%, at least 99%, at least 99.5%, at least 99.9%, at least 99.99%, or 100%.

In some variations, bio-content (also referred to as "bio-based content") can be determined based on the following: % Bio-content or Bio-based content=[Bio (Organic) Carbon]/[Total (Organic) Carbon]*100%, as determined by ASTM D6866 (Standard Test Methods for Determining the Bio-based Content of Solid, Liquid, and Gaseous Samples Using Radiocarbon Analysis).

The bio-content of the polymers may depend on the bio-content of the β-lactone used. For example, in some variations of the methods described herein, the β-lactone used to produce the polymers described herein may have a bio-content of greater than 0%, and less than 100%. In certain variations of the methods described herein, the β-lactone used to produce the polymers described herein may have a bio-content of at least 10%, at least 20%, at least 30%, at least 40%, at least 50%, at least 60%, at least 70%, at least 80%, at least 90%, at least 95%, at least 96%, at least 97%, at least 98%, at least 99%, at least 99.5%, at least 99.9%, at least 99.99%, or 100%. In certain variations, β-lactone derived from renewable sources is used. In other variations, at least a portion of the β-lactone used is derived from renewable sources, and at least a portion of the β-lactone is derived from non-renewable sources.

The biobased-content of the β-propiolactone may depend on, for example, the bio-content of the ethylene oxide and carbon monoxide used. In some variations, both ethylene oxide and carbon monoxide are derived from renewable sources.

In some variations of the foregoing, the polymer has a biodegradability of at least 10%, at least 20%, at least 30%, at least 40%, at least 50%, at least 60%, at least 70%, at least 80%, at least 90%, at least 95%, at least 96%, at least 97%, at least 98%, at least 99%, at least 99.5%, at least 99.9%, at least 99.99%, or 100%.

In some variations of the foregoing, biodegradable is as defined and determined based on ASTM D5338-15 (Standard Test Method for Determining Aerobic Biodegradation of Plastic Materials Under Controlled Composting Conditions, Incorporating Thermophilic Temperatures).

An object of the present invention is to provide absorbent sanitary articles having improved properties in handling fluid wastes while maintaining characteristics of biodegradability and biobased content.

Numerous other features and advantages of the present invention will appear from the following description.

While this description is susceptible to various modifications and alternative forms, specific exemplary embodiments thereof have been shown by way of example and have herein been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

DETAILED DESCRIPTION OF EMBODIMENTS

The following description includes preferred embodiments of the present invention which are directed to biodegradable polyol polymers having higher biobased carbon content. It should be recognized, however, that such description is not intended as a limitation on the scope of the present disclosure but is instead provided as a description of exemplary aspects.

Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March March's *Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987; the entire contents of each of which are incorporated herein by reference.

The term "polymer", as used herein, refers to a molecule of high relative molecular mass, the structure of which comprises the multiple repetitions of units derived, actually or conceptually, from molecules of low relative molecular mass. In some aspects, a polymer is comprised of only one monomer species (e.g., polyEO). In some aspects, a polymer is a copolymer, terpolymer, heteropolymer, block copolymer, or tapered heteropolymer of one or more epoxides.

As used herein, the term "catalyst" refers to a substance the presence of which increases the rate of a chemical reaction, while not being consumed or undergoing a permanent chemical change itself.

Biodegradability and biodegradable refer to the ability of a material to be broken down (decomposed) rapidly by the action of living organisms such as bacteria, fungi, microorganisms or other biological means wherein rapidly is typically less than 10 years, 5 years, for 2 years.

Sustainable material and sustainable polymer mean a biodegradable material and polymer, respectively, that is derived at least in part from green sources and has a percentage of green substituents equal to a minimum of 10%, and more typically 20%, 50%, 75%, 90%, 95%, or 100% of the total amount of carbon and hydrogen in the material.

As used herein, the term "about" preceding one or more numerical values means the numerical value ±5%. It should be understood that reference to "about" a value or parameter herein includes (and describes) aspects that are directed to that value or parameter per se. For example, description referring to "about x" includes description of "x" per se.

Further, it should be understood that reference to "between" two values or parameters herein includes (and describes) aspects that include those two values or parameters per se. For example, description referring to "between x and y" includes description of "x" and "y" per se.

The mass fractions disclosed herein can be converted to wt % by multiplying by 100.

In preferred embodiments of the present invention, the sanitary article is a diaper, an adult incontinence product, a sanitary napkin, or a feminine hygiene product. In certain preferred embodiments, the sanitary articles may be formed according to one or more well-known configurations. The sanitary articles having well-known configurations may also include one or more adhesive fasteners and/or one or more elastic members comprised of one or more of the herein disclosed biodegradable polymers with higher biobased content. Further, the one or more adhesive fasteners and/or one or more elastic members may be formed according to one or more well-known configurations. In preferred embodiments, the sanitary article is bio-based and/or biodegradable.

Preferred embodiments of the present invention may include one or more polymers having a biobased content β-lactone as a monomer, intermediate, or reagent. The β-lactone monomers may be formed from carbonylation of an epoxide with carbon monoxide in the presence of a carbonylation catalyst. In certain preferred embodiments, the epoxide is ethylene oxide which may undergo a carbonylation reaction, with carbon monoxide, in the present of a carbonylation catalyst to produce a β-lactone. In some embodiments, the epoxide is selected from the group consisting of: propylene oxide, 1,2-epoxybutane, 2,3-epoxybutane, cyclohexene oxide, cyclopentane oxide, 1,2-epoxyhexane, 1,2-epoxydodecane, 2-cyclohexyloxirane, 3,3,3-Trifluoro-1,2-epoxypropane, styrene oxide, n-butyl glycidyl ether, tert-butyldimethylsilyl glycidyl ether, and benzyl glycidyl ether. In certain embodiments, the epoxide is ethylene oxide.

In some embodiments, the β-lactone may be β-butyrolactone, β-valerolactone, β-heptanolactone, β-tridecanolactone, cis-3,4-dimethyloxetan-2-one, 4-(but-3-en-1-yl)oxetan-2-one, 4-(butoxymethyl)-2-oxetanone, 4-[[[(1,1-dimethylethyl)dimethylsilyl]oxy]methyl]-2-oxetanone, 4-[(2-propen-1-yloxy)methyl]-2-oxetanone, or 4-[(benzoyloxy)methyl]-2-Oxetanone. In certain embodiments, the β-lactone is β-propiolactone.

Preferred embodiments of the sanitary articles include a topsheet comprising a biodegradable polyester polyol polymer. The biodegradable polyester polymer may be foamed to form a lattice having pores. The foam may be impregnated by superabsorbent polymer. In some embodiments, the super absorbent polymer may be heterogeneously dispersed within the foam so that it is mechanically held in place. In some embodiments, the superabsorbent polymer may be impregnated so that it is heterogeneously contained within the pores of the foam.

In preferred embodiments, the monomers of the polyester polyol polymers may be produced from renewable and/or recycled sources of carbon. In certain preferred embodiments, β-lactone monomers of the polyester polyol polymers may be produced from carbonylation of an epoxide with carbon monoxide. The epoxide sources and carbon monoxide sources may have high biobased carbon content. The β-lactone monomers may be reacted with monomers with hydroxyl functional groups such as simple alcohols, diols, triols, and sugar alcohols with high biobased carbon content. Advantageously, the polyester polyol polymers of the present invention may have increased biodegradability and may have increased biobased content. In certain preferred embodiments, the polyols may be reacted with β-lactone monomers with higher biobased content to produce modified polyols with higher biobased content.

In certain preferred embodiments, the polyester polyol polymers may include multiple carbonyl, carbonate, acetal, ether, nitrile, urethane, urea, imide, anhydride, phosphate, and/or cyanocrylate functional groups in the main chain for facilitating biodegradability. The polyol includes cross-links between polymer main chains allowing for the formation of pores in a three-dimensional structure. The composition of the polyol and the cross-linking molecules may determine the pore size and general structural properties of the polyol lattice. In some embodiments, cross-linking agents may include vinyl groups, for example, N,N'-methylene-bisacrylamide, N,N'-ethylene-bis-methacrylamide, hexamethylene-bis-acrylamide, triallyl amine, ethylene glycol dimethacrylate, trimethylolpropane trimethacrylate, pentaerythritol trimethacrylate, and ally methacrylate.

The morphology of the topsheet may be created by any method that will produce a physical mixture wherein discrete particles of superabsorbent polymer are interspersed as a physical mixture throughout a matrix of the biodegradable polyester polyol polymer. The physical mixture may be homogenous. Alternately the physical mixture may be non-homogenous as previously described such that the concentration of the discrete particles varies in different regions of the topsheet. The size of the discrete particles may vary from as small 20 micrometers or less to as large as the desired thickness of the top layer. Preferably the volume and/or the mass of the particles will be less than the respective volume or mass of the matrix. In the case of a topsheet polymer that defines a lattice or a pore size, the pore size and general structural properties of the polyol lattice may determine a capacity for superabsorbent polymer and inter-lattice dispersion distance for superabsorbent polymer.

In those aspects that provide the topsheet in the form of a foam having pores, foam pores will generally be spherical in shape. The size or "diameter" of such spherical pores of polyester polyol polymer foams will not necessarily be the same size for all pores but rather may be characterized as a mean pore size, i.e., mean pore diameter. In certain aspects of the invention the pore volume may vary from face to face of the top sheet to provide regions of different pore density or pore sizes. In certain aspects of the invention each region of pores may possess a different mean pore size. Each region may also possess a different distribution about that mean, e.g., one region may contain pores of mean diameter of 130 micrometers with 90% of all definable pores being between about 80 micrometers and 180 micrometers, while the distinct region may contain pores of mean diameter of 50 micrometers with 90% of all definable pores being between about 20 micrometers and 80 micrometers.

In certain embodiments, the polyester polyol polymer lattice may be formed by conventional foaming techniques for producing foam structures such as blowing. In some embodiments, the foam structure of interconnected open-cells may include at least two distinct regions of pore sizes. Foams having larger pore sizes may acquire fluid quickly but may not distribute fluid sufficiently against the force of gravity or store fluid effectively. Conversely, foams having smaller pore sizes may wick fluid against the force of gravity and contain the fluid, keeping the fluid from contacting the skin of the wearer. Advantageously, such heterogeneous foams have various applications, such as fluid absorption and insulation.

Preferred foams of the present invention will have one or more regions of pores suitable for liquid absorption having a mean pore diameter of from about 20 to about 200 micrometers, preferably from about 50 to about 190 micrometers, and most preferably from about 80 to about 180 micrometers. These foams will also preferably have one or more liquid wicking regions having a mean cell diameter of not more than about 50 micrometers, preferably from about 5 to about 35 micrometers.

In certain preferred embodiments, the foam may be impregnated with superabsorbent polymer. In certain embodiments, the superabsorbent polymer may be impregnated in the pores of the polyester polyol polymer lattice. In some embodiments, the superabsorbent polymer may be more highly concentrated in a region adjacent and proximate the absorbent core. Advantageously, embodiments of the present invention may more effectively wick liquids away from one or more body parts of a biological organism and store the liquids while maintaining characteristics of biodegradability and biobased content.

Preferred embodiments of the sanitary articles include an absorbent core comprised of superabsorbent polymer. The superabsorbent polymer may include a cross-linked and/or partially neutralized polyacrylic acid polymer, including cross-linked polyacrylic acids or cross-linked starch-acrylic acid graft polymers. The superabsorbent polymers may absorb large amounts of liquids including bodily fluids, such as urine or blood, swelling and retaining the aqueous liquids under a certain pressure in accordance with the general definition of a superabsorbent polymer.

In certain embodiments, the superabsorbent polymers may be prepared by neutralizing unsaturated carboxylic acids or derivatives thereof, such as acrylic acid, alkali metal (e.g., sodium and/or potassium) or ammonium salts of acrylic acid, alkyl acrylates, and the like in the presence of a caustic treatment, such as sodium hydroxide, and then polymerizing the product with a relatively small amount of an internal, or monomeric, cross-linker such as a di- and/or poly-functional monomer. The di- and/or poly-functional monomer materials may also serve as internal cross-linking agents to lightly cross-link the polymer chains. The cross-links may render the superabsorbent polymers water-insoluble, yet water absorbent. These lightly cross-linked superabsorbent polymers contain a multiplicity of carboxyl groups attached to the polymer backbone. Carboxyl groups may generate an osmotic driving force for the absorption of liquids by the cross-linked polymer network.

In certain preferred embodiments, the superabsorbent polymer may be formed by combining $\beta$-propiolactone with a metal compound to produce acrylic acid, a salt thereof, or a combination thereof; and polymerizing the acrylic acid, a salt thereof, or a combination thereof, with a polymerization initiator and preferably a cross-linker to produce the superabsorbent polymer. In some variations of the foregoing, the polymerizing is performed neat or in a non-aqueous medium. In some variations, the metal compound is M, M, $M_2O$, MOH, or $M^+(CH_2=CHCOO^-)$, or a combination thereof.

In certain preferred embodiments, the superabsorbent polymer may be formed by combining $\beta$-propiolactone with a metal compound to produce acrylic acid, a salt thereof, or a combination thereof; and polymerizing the acrylic acid, a salt thereof, or a combination thereof, with a polymerization initiator and preferably a cross-linker to produce the superabsorbent polymer. In some variations of the foregoing, the polymerizing is performed neat or in a non-aqueous medium. In some variations, the metal compound is M, $M_2O$, MOH, or $M^+(CH_2=CHCOO^-)$, or a combination thereof.

In certain embodiments, the superabsorbent polymer may be produced by methods or processes comprising:

a) polymerizing $\beta$-propiolactone with an ionic initiator in a reactor to produce a polymer intermediate, wherein the polymer intermediate has a polyacrylic acid backbone and a plurality of polypropiolactone side chains;

b) increasing the temperature of the reactor to produce acrylic acid from at least a portion of the side chains in the polymer intermediate, and to produce acrylate polymer from at least a portion of the polymeric backbone of the polymer intermediate by thermolysis of the polymer intermediate;

c) adding a metal compound of formula M, $M_2O$, MOH, or $M^+(CH_2=CHCOO^-)$, or a combination thereof, to the reactor to at least partially neutralize the acrylic acid in the reactor to produce a mixture, wherein the mixture in the reactor comprises acrylic acid and $M^+(CH_2=CHCOO^-)$, wherein M is a Group I metal; and d) polymerizing at least a portion of the mixture in the reactor to produce the polymer, wherein the polymer comprises repeating units of

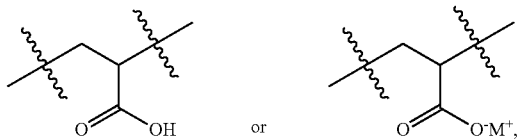

or a combination thereof.

In some variations of the foregoing, steps (c) and (d) are performed neat or in a non-aqueous medium. In some embodiments, the polymer is cross-linked. Cross-linking agents may include vinyl groups, for example, N,N'-methylene-bisacrylamide, N,N'-ethylene-bis-methacrylamide, hexamethylene-bis-acrylamide, triallyl amine, ethylene glycol dimethacrylate, trimethylolpropane trimethacrylate, pentaerythritol trimethacrylate, and ally methacrylate. Preferred embodiments of the processes disclosed provide for superabsorbent polymer which is bio-based and/or bio-degradable.

In preferred embodiments, the backsheet of the present invention includes poly-lactone, polybutylene succinate, and/or polybutylene succinate derivatives. In certain preferred embodiments, the backsheet may be comprised of poly-lactone polymers comprising β-lactone monomers having linear chains of repeating $(O(CH_2)_2CO)_X$ monomer units containing carbon and oxygen atoms provided by a β-lactone feed produced from the carbonylation of an epoxide containing carbon atoms that originate from a biobased source. In some embodiments, the poly-lactone polymers include cross-linking agents such as vinyl groups, for example, N,N'-methylene-bisacrylamide, N,N'-ethylene-bis-methacrylamide, hexamethylene-bis-acrylamide, triallyl amine, ethylene glycol dimethacrylate, trimethylolpropane trimethacrylate, pentaerythritol trimethacrylate, and ally methacrylate. In certain preferred embodiments, the poly-lactones may have or be modified to have a higher degree of hydrophobicity.

The poly-lactone polymers of the present invention may have the following formula:

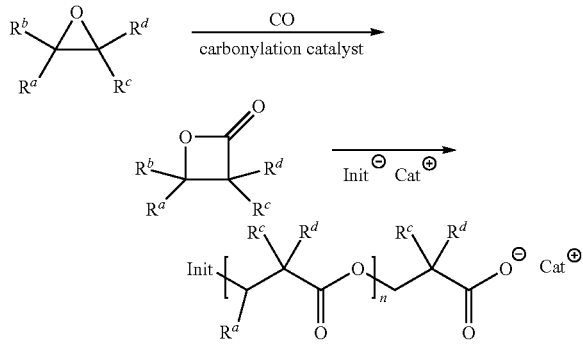

where $Init^-$ is an anionic nucleophile and $Cat^+$ is cation.

The suitable anionic nucleophiles include $R^xO^-$, $R^xC(=O)O^-$, $R^xS^-$, $R^xO(C=O)O^-$, halide (e.g., $Br^-$, $I^-$, $Cl^-$), $R^x(SO_2)O^-$ and $PR^x{}_3O^-$, wherein each $R^x$ is, independently, selected from hydrogen, optionally substituted aliphatic, optionally substituted heteroaliphatic, optionally substituted aryl and optionally substituted heteroaryl.

In certain embodiments, $Init^-$ is $R^xC(=O)O^-$, $R^x$ is selected from optionally substituted aliphatic, fluorinated aliphatic, optionally substituted heteroaliphatic, optionally substituted aryl, fluorinated aryl, and optionally substituted heteroaryl. For example in certain aspects $Init^-$ may be $CH_2=CHCO_2^-$, $CH_3CO_2^-$, or $CF_3CO_2^-$.

In certain embodiments, $Init^-$ is $R^xO^-$, $R^x$ is selected from optionally substituted aliphatic, optionally substituted heteroaliphatic, optionally substituted aryl, and optionally substituted heteroaryl. For example, in certain aspects $Init^-$ is hydroxide, methoxide, or ethoxide.

In certain embodiments, $Cat^+$ is selected from the group consisting of $Li^+$, $Na^+$, $K^+$, $Mg^{2+}$, $Ca^{2+}$, and $Al^{3+}$. In some embodiments, $Cat^+$ is $Na^+$. In some aspects, $Cat^+$ is an organic cation. In some variations, the organic cation is selected from the group consisting of quaternary ammonium, imidazolium, and bis(triphenylphosphine)iminium. In some variations, the quaternary ammonium cation is tetraalkyl ammonium.

The embodiments described herein are not intended to be limited to the aspects shown, but are to be accorded the widest scope consistent with the principles and features disclosed herein.

What is claimed is:

1. A biodegradable sanitary article, comprising:
   a) a topsheet comprising a biodegradable polyester polyol polymer with a heterogeneous dispersion of a biodegradable superabsorbent polymer retained therein, wherein the biodegradable polyester polyol polymer in the topsheet has pores impregnated with the biodegradable superabsorbent polymer;
   b) an absorbent core comprising a biodegradable superabsorbent polymer having an inner side positioned adjacent to and fixed with respect to the topsheet; and,
   c) a backsheet comprising a biodegradable poly-lactone polymer positioned adjacent to an outer side of the absorbent core and fixed with respect to the absorbent core.

2. The biodegradable sanitary article of claim 1, wherein the superabsorbent polymer is dispersed in the topsheet as discrete particles.

3. The biodegradable sanitary article of claim 1, wherein the topsheet has:
   i. an absorbent face positioned adjacent to the absorbent core and a corporeal face on an outward face of the sanitary article; and
   ii. a concentration of superabsorbent polymer near the corporeal face that is greater than the concentration of superabsorbent polymer near the absorbent face.

4. The biodegradable sanitary article of claim 2, wherein the discrete particles have an average diameter of greater than 20 micrometers and less than the average thickness of the topsheet.

5. The biodegradable sanitary article of claim 1, wherein the biodegradable polyol polyester polymer in the topsheet comprises a foam.

6. The biodegradable sanitary article of claim 1, wherein 90% of the pores have a mean diameter of at least 20 micrometers and no more than 180 micrometers.

7. The biodegradable sanitary article of claim 1, wherein the topsheet has an absorbent face positioned adjacent to the absorbent core and a corporeal face on an outward face of the biodegradable sanitary article, and wherein the topsheet comprises at least a first pore region adjacent and proximate to the corporeal face and a second pore region adjacent and proximate to the absorbent face.

8. The biodegradable sanitary article of claim 7, wherein the first pore region has smaller pore sizes than the second pore region.

9. The biodegradable sanitary article of claim 8, wherein the second pore region comprises pores having a higher concentration of superabsorbent polymer than the first pore region.

10. The biodegradable sanitary article of claim 1, wherein the biodegradable poly-lactone polymer in the backsheet has or is modified to have a hydrophobic characteristic.

11. The biodegradable sanitary article of claim 1, wherein the biodegradable sanitary article comprises one or more elastic members formed from one or more of a biodegradable polyester polyol polymer, a biodegradable polyacrylic acid derivative, and a biodegradable poly-lactone polymer.

12. The biodegradable sanitary article of claim 1, wherein the biodegradable sanitary article comprises one or more adhesive fasteners formed from one or more of a biodegradable polyester polyol polymer, a biodegradable polyacrylic acid derivative, and a biodegradable poly-lactone polymer.

13. The biodegradable sanitary article of claim 1, wherein the biodegradable polyester polyol polymer of the topsheet comprises one or more carbonyl, carbonate, acetal, ether, nitrile, urethane, urea, imide, anhydride, phosphate, or cyanocrylate functional groups, or any combination thereof.

14. The biodegradable sanitary article of claim 1, wherein the biodegradable polyester polyol polymer of the topsheet comprises cross-links between polymer main chains allowing for the formation of pores in a three-dimensional structure.

15. The biodegradable sanitary article of claim 1, wherein the biodegradable poly-lactone polymer of the backsheet comprises poly-lactone, polybutylene succinate, or polybutylene succinate derivatives, or any combination thereof.

16. The biodegradable sanitary article of claim 1, wherein the biodegradable superabsorbent polymer of the absorbent core comprises a polymer comprising β-propiolactone monomers.

17. A biodegradable sanitary article, comprising:
  a) a topsheet comprising a biodegradable polyester polyol polymer lattice having pores impregnated with a heterogenous dispersion of a biodegradable superabsorbent polymer;
  b) an absorbent core comprising a biodegradable superabsorbent polymer having an inner side positioned adjacent to and fixed with respect to the topsheet; and,
  c) a backsheet comprising a biodegradable poly-lactone polymer positioned adjacent to an outer side of the absorbent core and fixed with respect to the absorbent core.

18. The biodegradable sanitary article of claim 17, wherein the topsheet comprises an absorbent face positioned adjacent to the absorbent core and a corporeal face.

19. The biodegradable sanitary article of claim 18, wherein the topsheet comprises at least a first pore region adjacent and proximate to the corporeal face and a second pore region adjacent and proximate to the absorbent face.

20. The biodegradable sanitary article of claim 19, wherein the first pore region has smaller pore sizes than the second pore region.

21. The biodegradable sanitary article of claim 20, wherein the second pore region comprises pores having a higher concentration of superabsorbent polymer than the first pore region.

22. The biodegradable sanitary article of claim 17, wherein the biodegradable poly-lactone polymer of the backsheet has or is modified to have a hydrophobic characteristic.

* * * * *